United States Patent
Katra

(10) Patent No.: US 11,039,768 B2
(45) Date of Patent: Jun. 22, 2021

(54) SYSTEM AND METHOD FOR NON-INVASIVE MONITORING OF HEMOGLOBIN

(71) Applicant: Medtronic Monitoring, Inc., San Jose, CA (US)

(72) Inventor: Rodolphe Katra, Blaine, MN (US)

(73) Assignee: Medtronic Monitoring, Inc., San Jose, CA (US)

(*) Notice: Subject to any disclaimer, the term of this patent is extended or adjusted under 35 U.S.C. 154(b) by 570 days.

(21) Appl. No.: 15/866,036

(22) Filed: Jan. 9, 2018

(65) Prior Publication Data

US 2019/0209060 A1   Jul. 11, 2019

(51) Int. Cl.
| | |
|---|---|
| *A61B 5/1455* | (2006.01) |
| *A61B 5/145* | (2006.01) |
| *A61B 5/02* | (2006.01) |
| *A61B 5/00* | (2006.01) |

(52) U.S. Cl.
CPC ........ *A61B 5/14546* (2013.01); *A61B 5/0071* (2013.01); *A61B 5/02028* (2013.01); *A61B 5/1455* (2013.01); *A61B 5/14551* (2013.01); *A61B 5/0082* (2013.01); *A61B 5/6838* (2013.01); *A61B 2562/0233* (2013.01)

(58) Field of Classification Search
CPC . A61B 5/0205; A61B 5/1455; A61B 5/14551; A61B 5/14552; A61B 5/14546; A61B 5/02028; A61B 5/0071; A61B 5/0082; A61B 5/6838

See application file for complete search history.

(56) References Cited

U.S. PATENT DOCUMENTS

| | | | |
|---|---|---|---|
| 5,372,136 A | 12/1994 | Steuer et al. | |
| 5,377,674 A | 1/1995 | Kuestner | |
| 5,377,675 A * | 1/1995 | Ruskewicz | ........ A61B 5/14542 600/341 |
| 5,692,503 A | 12/1997 | Kuenstner et al. | |

(Continued)

FOREIGN PATENT DOCUMENTS

| | | |
|---|---|---|
| WO | 9313706 A2 | 7/1993 |
| WO | 2003077761 A1 | 9/2003 |

(Continued)

OTHER PUBLICATIONS

Notification of Transmittal of the International Search Report and the Written Opinion of the International Searching Authority, or the Declaration for PCT/IB2019/050235.

(Continued)

*Primary Examiner* — Chu Chuan Liu
(74) *Attorney, Agent, or Firm* — Shumaker & Sieffert, P.A.

(57) ABSTRACT

A method of non-invasively monitoring hemoglobin concentration includes providing incident light to patient tissue at a first excitation wavelength. The method further includes monitoring a first emission response at a first emission wavelength, wherein the first emission wavelength is selected to correspond with a maximum of the emission response, and monitoring a second emission response at a second emission wavelength, wherein the second emission wavelength is selected to correspond with a minimum of the emission response. A hemoglobin concentration is calculated based on a ratio of the first emission response to the second emission response.

17 Claims, 11 Drawing Sheets

(56) References Cited

U.S. PATENT DOCUMENTS

| | | | |
|---|---|---|---|
| 6,064,474 | A | 5/2000 | Lee et al. |
| 6,526,298 | B1* | 2/2003 | Khalil .............. A61B 5/0059 |
| | | | 600/310 |
| 6,606,509 | B2 | 8/2003 | Schmitt |
| 6,728,560 | B2 | 4/2004 | Kollias et al. |
| 7,139,598 | B2 | 11/2006 | Hull et al. |
| 8,078,243 | B2 | 12/2011 | Ediger et al. |
| 8,121,671 | B2 | 2/2012 | Hull et al. |
| 8,131,332 | B2 | 3/2012 | Maynard et al. |
| 8,172,459 | B2 | 5/2012 | Abreu |
| 8,238,993 | B2 | 8/2012 | Hull et al. |
| 8,320,981 | B1 | 11/2012 | Mayer et al. |
| 8,346,332 | B2 | 1/2013 | Kuhn et al. |
| 8,480,581 | B2 | 7/2013 | Zhang et al. |
| 8,571,620 | B2 | 10/2013 | Cinbis et al. |
| 8,676,283 | B2 | 3/2014 | Matter et al. |
| 2002/0038079 | A1 | 3/2002 | Steuer et al. |
| 2002/0082489 | A1* | 6/2002 | Casciani .............. A61B 5/1464 |
| | | | 600/338 |
| 2002/0165439 | A1 | 11/2002 | Schmitt |
| 2003/0018241 | A1* | 1/2003 | Mannheimer ...... A61B 5/14551 |
| | | | 600/300 |
| 2004/0225207 | A1 | 11/2004 | Bae et al. |
| 2007/0156036 | A1 | 7/2007 | Pilon et al. |
| 2008/0214911 | A1 | 9/2008 | Forstner |
| 2009/0118666 | A1 | 5/2009 | Blomqvist et al. |
| 2010/0110416 | A1 | 5/2010 | Barrett et al. |
| 2010/0185252 | A1 | 7/2010 | Bjorling et al. |
| 2010/0280499 | A1 | 11/2010 | Yodfat et al. |
| 2010/0298675 | A1 | 11/2010 | Al-Ali et al. |
| 2013/0178724 | A1 | 7/2013 | Ting et al. |
| 2013/0217984 | A1 | 8/2013 | Graaff et al. |
| 2015/0073243 | A1 | 3/2015 | Taub et al. |
| 2015/0201839 | A1 | 7/2015 | Kang et al. |
| 2015/0245799 | A1 | 9/2015 | Gretz et al. |
| 2016/0061810 | A1 | 3/2016 | Kim et al. |
| 2016/0371452 | A1 | 12/2016 | Landrum et al. |
| 2019/0209055 | A1 | 7/2019 | Katra |
| 2019/0209061 | A1 | 7/2019 | Katra |

FOREIGN PATENT DOCUMENTS

| | | |
|---|---|---|
| WO | 2011159148 A2 | 12/2011 |
| WO | 2012005696 A1 | 1/2012 |

OTHER PUBLICATIONS

Notification of Transmittal of the International Search Report and the Written Opinion of the International Searching Authority, or the Declaration for PCT/IB2019/050236 dated Apr. 26, 2019.

Notification of Transmittal of the International Search Report and the Written Opinion of the International Searching Authority, or the Declaration for PCT/IB2019/050238 dated Jun. 26, 2019.

Jeon, et al., "Noninvasive Total Hemoglobin Measurement", Journal of Biomedical Optics, 7(1), Jan. 2020, 45-50.

International Search Report and Written Opinion of International Application No. PCT/IB2019/050235, dated Apr. 26, 2019, 13 pp.

Carneiro, "Haemoglobin and haematocrit: is the threefold conversion valid for assessing anaemia in malaria-endemic settings", Malaria Journal 2007, 6:67.

Ciobanu, et al., "Fluorophores advanced glycation end products (AGEs)-to-NADH ratio is predictor for diabetic chronic kidney and cardiovascular disease", J Diabetes Complications. Sep.-Oct. 2015;29(7):893-7. doi: 10.1016/j.idiacomp.2015.06.006. Epub Jun. 16, 2015.

Ediger, et al., "Noninvasive Optical Detection of Impaired Glucose Tolderance: A Comparison Against FPG and A1C", 62, Review of Endocrinology, June 2007.

Hartog, et al., "Advanced glycation end-products (AGEs) and hearth failure: Pathophysiology and clinical implications", European Journal of Heart Failure (2007) 1146-1155.

Li, et al., "Advanced glycation end products bisphasicallu modulate bone resorption in osteoclast-like cells", Am J Physiol Endocrinol Metab 310: E355-E366, 2016.

Lowndes, "Blood interference in fluorescence spectrum—Experiment, analysis and comparison with intra-operative measurements on brain tumor", Linkoping University, Jul. 9, 2010, 42 pages.

Pandey, et al., "Emerging trends in optical sensing of glycemic markers for diabetes monitoring", Trends Analyt Chem. Jan. 1, 2015; 64: 100-108.

Rabe, et al., "Measurement of Transcutaneous Hemoglobin Concentration by Noninvasive White-Light Spectroscopy in Infants", Pediatrics, Oct. 2005, vol. 116 / Issue 4 (abstract).

Wong, et al., "Augmentation of the Neutrophil Respitory Burst Through the Action of Advanced Glycation End Products", Diabetes Sep. 2002; 51(9): 2846-2853.

Anand, et al., "Anemia and Change in Hemoglobin Over Time Related to Mortality and Morbidity in Patients With Chronic Heart Failure", Results From Val-HeFT. Circ. 2005; 112: 1121-1127.

Blackwell, et al., "In Vivo Time-Resolved Autofluorescense Measurements to Test for Glycation of Human Skin", University of California Postprints, 2008, Paper 2665.

De Denus, et al., "Temporal Variations in Hematocrit Values in Patients with Left Ventricular Dysfunction: Relationship with Cause-Specific Mortality and Morbidity and Optimal Monitoring—Further Insights from SOLVD", Can. J. Cardiol 2008, 24: 45-48.

Heike, et al., "Measurement of Transcutaneous Hemoglobin Concentration by", 2005;116;841-843.

Horecker, "The Absorption Spectra of Hemoglobin and its Deriavitives in the Visible", Dec. 3, 1942.

McMurdy, et al., "Noninvasive Optical, Electrical, and Acoustic Methods of Total", Clinical Chemistry 54:2, 264-272 (2008).

Office Action from U.S. Appl. No. 15/866,118, dated Dec. 3, 2020, 14 pp.

Amendment in Response to Office Action dated Oct. 13, 2020, from U.S. Appl. No. 15/866,160, filed Jan. 6, 2021, 8 pp.

Office Action from U.S. Appl. No. 15/866,160, dated Oct. 13, 2020, 12 pp.

Amendment in Response to Office Action dated Dec. 3, 2020, from U.S. Appl. No. 15/866,118, filed Feb. 25, 2021, 10 pp.

Final Office Action from U.S. Appl. No. 15/866,118, dated Apr. 5, 2021, 12 pp.

\* cited by examiner

SYSTEM AND METHOD FOR NON-INVASIVE MONITORING OF HEMOGLOBIN

TECHNICAL FIELD

This invention relates generally to patient diagnosis and monitoring, and in particular non-invasive diagnosis and monitoring of hemoglobin concentrations.

BACKGROUND

Hemoglobin (Hb) is the iron-containing protein found in blood and is the component responsible for transporting gases throughout the body, such as oxygen and carbon dioxide. Measuring hemoglobin concentration is a useful tool in screening patients for diseases such as anemia. Typically, hemoglobin concentration measurements require a blood sample to be taken from a patient, which is sent to a lab for analysis to isolate and measure the concentration of Hb in the patient's blood. Results typically take 1-2 days to obtain, and are based on the Hb levels in the patient at the time blood is drawn. As a result, it is not feasible to monitor Hb levels continuously over long periods of time.

It would therefore be advantageous to develop a device that is capable of detection and long-term monitoring of Hb concentration (as well as other blood components such as hematocrit, HbA1C, advanced glycation end (AGE) products), which would allow for the detection of acute conditions as well as chronic conditions that change slowly over time.

SUMMARY

A method of non-invasively monitoring hemoglobin concentration includes providing incident light to patient tissue at a first excitation wavelength. The method further includes monitoring a first emission response at a first emission wavelength, wherein the first emission wavelength is selected to correspond with a maximum or dominant wavelength of the emission response, and monitoring a second emission response at a second emission wavelength, wherein the second emission wavelength is selected to correspond with a minimum or a significant wavelength of the emission response. A hemoglobin concentration is calculated based on a ratio of the first emission response to the second emission response.

DETAILED DESCRIPTION

Figure 1:
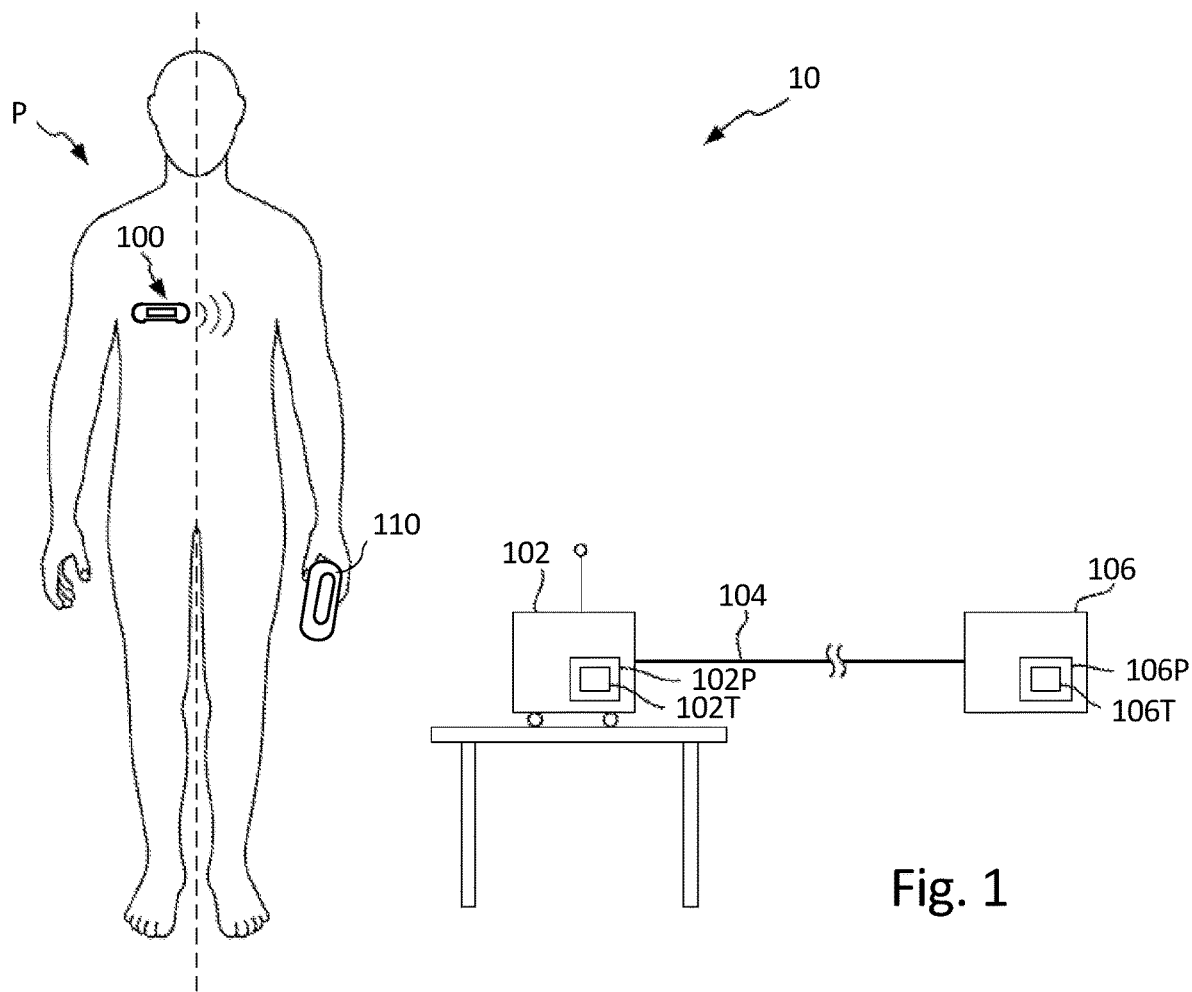
FIG. 1 illustrates a schematic view of a patient and a patient monitoring system, according to some embodiments.

FIG. 1 illustrates a patient P and a monitoring system 10 for non-invasive monitoring of blood concentration levels (e.g., hemoglobin, oxyhemoglobin, deoxyhemoglobin, etc.) In the embodiment shown in FIG. 1, monitoring system 10 comprises a patient medical device 100 and/or 110, gateway 102, and remote monitoring center 106. In the embodiment shown in FIG. 1, patient medical device 100 is an adherent device that attaches to the skin of the patient, and patient medical device 110 is a clip that fits over a patient's finger. In other embodiments, patient medical device may include implantable devices, insertable devices, injectable devices, and/or wearable devices such as a Holter monitor (collectively referred to as a medical device). In each example, the patient medical device utilizes optical components to monitor blood concentration levels of the patient. In some embodiments, patient medical device 100 includes one or more additional sensors for monitoring one or more additional physiological parameters of the patient, such as activity, orientation, cardiac activity, hydration, etc.

In the embodiment shown in FIG. 1, medical device 100 is adhered to the thorax T of patient P, which allows for the monitoring of additional physiological parameters, such as ECG, hydration, activity, etc. In many embodiments, the device may adhere to one side of the patient, from which side data can be collected. A benefit of utilizing an adherent device, implantable, injectable, and/or wearable device is that it may be utilized to collect physiological data from the patient while the patient goes about normal day-to-day activities outside of a hospital setting. A medical device clipped to a patient's finger, such as medical device 110, is not worn throughout the day by a patient, but may be useful in applications such as these due to the relative ease in applying the clip to a patient's finger in order to take a reading. That is, rather than wearing the device for an extended period of time, a patient may periodically clip the device to the patient's finger for a few moments (e.g., seconds) in order to non-invasively measure a blood concentration level (e.g., oxy-Hb, deoxy-Hb), and then remove.

As discussed above, in some embodiments, the medical device may monitor a number of physiological parameters associated with patient P, including optical signals utilized to determine blood concentration levels, electrocardiogram (ECG) signals utilized to detect rhythm abnormalities such as tachycardia and/or bradycardia as well as activity level data, posture, bio-impedance, etc. Analysis of one or more of these physiological parameters may be done locally by the medical devices 100 or 110, or remotely by gateway 102 and/or remote monitoring center 106 (or similar platform separate from the local medical device 100). In one embodiment, gateway 102 is a stand-alone device installed—typically—in the patient's home. In other embodiments, gateway 102 may be a patient device (such as a smartphone, tablet, or computer) capable of storing and executing one or more applications designed to process signals received from medical devices 100 and/or 110. Non-invasive monitoring of blood concentration levels relies on one or more optical sensors positioned on the medical device to provide an excitation source (e.g., light) to patient tissue and monitor the emission response (e.g., light emitted by the patient tissue as a result of reflection, fluorescence, absorbance of the incident light). For example, in one embodiment one or more light sources associated with the medical device direct incident light to patient tissue. In addition, one or more photodetectors associated with the medical device receives light emitted from the patient at a particular emission wavelength associated with the photodetector (e.g., wavelengths of 590 nm). The photodetector converts the measured emission (i.e., optical signal) to an electrical signal that is representative of the amplitude or strength of the emitted light. As discussed in more detail below, analysis of the detected optical signal can be utilized to monitor blood concentration levels. In some embodiments, the analysis is performed locally by the medical device 100 or 110, while in other embodiments the monitored optical signal is transmitted to a gateway 102 or remote center 106 for analysis to detect blood concentration levels.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent devices 100 or 110 are read by human experts to verify accuracy. Reports may then be generated at remote monitoring center 106 for communication to the patient's physician or care provider. As discussed above, in other embodiments gateway 102 may be implemented with a user device such as a smartphone, tablet, or computer capable of storing and executing one or more applications capable of processing data received from medical devices 100 and/or 110, as well as communicating the received data to remote monitoring center 106.

In an exemplary embodiment, the monitoring system comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including optical signals—monitored by medical device 100 may be analyzed by one or more of the distributed processors included as part of medical device 100, gateway 102, and/or remote monitoring center 106.

Figure 2A:
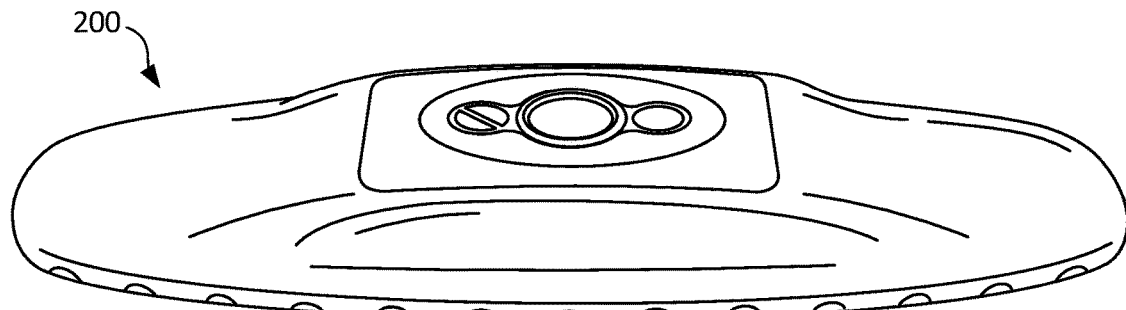
FIGS. 2A-2C are perspective views of an adherent monitoring device according to some embodiments.
Figure 2B:
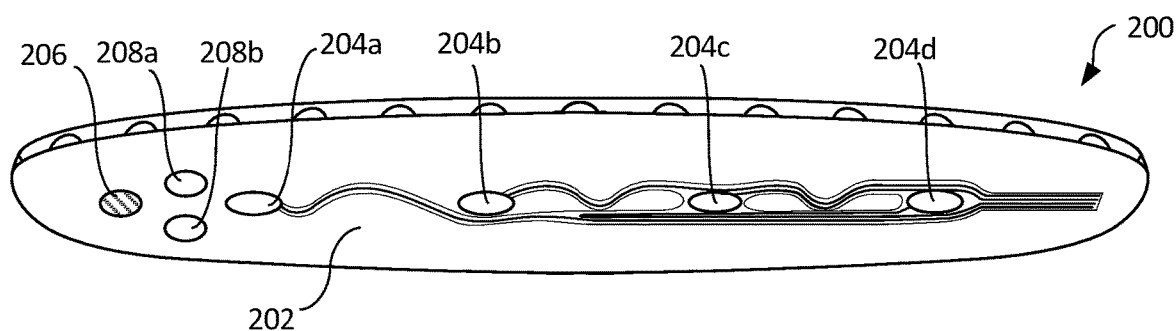
Figure 2C:
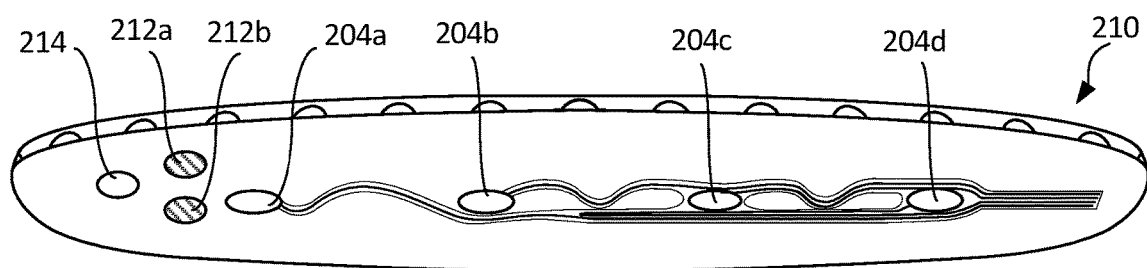

FIGS. 2A-2C are perspective views of an adherent monitoring device according to some embodiments. Adherent devices are adhered to the skin of a patient, and include one or more sensors utilized to monitor physiological parameters of the patient. Adherent devices are often-times utilized for long-term monitoring of ambulatory patients, allowing physiological parameters of the patient to be monitored over a period of time (e.g., days, weeks, months). Adherent devices therefore allow for both long-term monitoring of patients with chronic conditions (e.g., anemia) as well as monitoring and detection of acute incidences (e.g., carbon monoxide poisoning). This is in contrast with typical blood tests, which require blood be drawn by a lab and therefore do not allow for either long-term monitoring or detection of acute conditions.

The adherent device 200 illustrated in FIG. 2A illustrates the relatively low profile of adherent devices, which allows patients to wear the devices comfortably over a long period of time.

In the embodiment shown in FIG. 2B, a bottom surface 202 of adherent device 200 is shown, which includes a plurality of electrodes 204a-204d, at least one light emitter 206, and two photodetectors 208a, 208b. Electrodes 204a-204d are utilized to monitor electrical activity associated with the patient, including monitoring electrocardiogram (ECG) information and bio-impedance. The at least one light emitter 206 is utilized to generate an excitation signal (e.g., incident light) provided incident to patient tissue. Light provided by emitter 206 may be comprised of a plurality of wavelengths, including visible light, ultraviolet light (shorter wavelengths than visible light), and infrared light (longer wavelengths than visible light). In other embodiments, light provided by emitter 206 may be comprised of one or more selected wavelengths. Depending on the particular aspect/component of blood to be monitored (e.g., hemoglobin, oxyhemoglobin, deoxyhemoglobin, glycosylated hemoglobin A1c (HbA1c), hematocrit levels, etc.), different wavelengths of light may be selected in order to generate a particular emission response, which refers to how the incident light at a particular wavelength interacts with blood components via reflectance, absorbance, fluorescence, etc., which is represented by the light emitted from the patient. For example, hemoglobin is defined by an emission response to incident light provided at a particular wavelength.

In addition, the embodiment shown in FIG. 2B, the bottom surface 202 of adherent device 200 includes two or more photodetectors 208a, 208b. In this embodiment, each photodetector is configured to detect light at a particular emission wavelength. The wavelength selected is based on the emission response or morphology of the blood component being analyzed (e.g., hemoglobin, hematocrit, platelets, etc.). In a lab environment, the entire spectral response (e.g., all wavelengths) may be measured and analyzed. This is cost prohibitive though in an adherent device. Instead of monitoring all wavelengths, the embodiment shown in FIG. 2B selects two or more wavelengths to monitor. The wavelengths are selected based on the particular blood component being analyzed, and are selected to correlate with at least one maximum and at least one minimum of the emission response. Alternatively, the emission wavelength could be selected to reflect significant wavelength from the absorbance spectra of Hb. For example, hemoglobin is defined by a spectral response that includes a maximum at a wavelength of approximately 575 nm, and a minimum at a wavelength of approximately 560 nm. In this example, photodetector 208a may be configured to monitor an attribute (e.g., amplitude) of the emission response provided at 575 nm, and photodetector 208b may be configured to monitor an attribute (e.g., amplitude) of the emission response provided at 560 nm.

Based on the measured attribute of emitted light at select wavelengths, a ratio of the measured attributes is calculated, wherein the ratio provides a measure of the blood concentration component. A benefit of utilizing a ratio is that the measure is relatively immune to noise and external factors such as change in ambient light intensity, molecule concentrations, artifacts, light source instability, detector instability, and/or changes in placement of the sensor. For example, a measurement taken during the night in which little or no external light is available may provide an amplitude that is much lower than the amplitude measured if the patient is outside in the sun—in which light from the sun increases the measured amplitude at both the minimum and the maximum.

Although in the embodiment shown in FIG. 2B, a single emitter 206 is shown along with a pair of detectors 208a and 208b, in other embodiment a plurality of emitters may be utilized along with more than two detectors. In addition, although each emitter and detector is illustrated as a separate entity, in some embodiments the functions of an emitter and detector are included in a single device. Therefore, on one embodiment light source 206 may also include a photodetector 208. Photodetectors may be implemented with well-known imaging sensors such as CCD or CMOS image sensors.

In contrast with the embodiment shown in FIG. 2B, in which the number of detectors 208 was greater than the number of emitters 206, in other embodiments the number of emitters 206 may be greater than the number of detectors 208. For example, in the embodiment shown in FIG. 2C, rather than utilize a single light source or emitter and two or more detectors, adherent device 210 includes a pair of emitters 212a and 212b and a single photodetector 214. In this embodiment, each light source or emitter 212a and 212b provides incident light at a unique wavelength. Photodetector 214 monitors emissions at a single wavelength, selected to correspond with an emission response associated with first excitation wavelength, and an emission response associated with the second excitation wavelength.

In some embodiments, emitters 212a and 212b are controlled to generate incident light mutually exclusive of one another (e.g., one at a time). This allows detector 214 to measure the emission response associated with the first excitation wavelength and the emission response associated with the second excitation wavelength, separately. For example, in one embodiment emitter 212a is activated to provide incident light at a first wavelength. Photodetector 214 measures an attribute (e.g., amplitude) relating to the emission response at a given emission wavelength. Subsequently, emitter 212a is deactivated and emitter 212b is activated to provide incident light at a second wavelength. Photodetector 214 measures the attribute (e.g., amplitude) relating to the emission response at the same given emission wavelength. The ratio of the measured amplitudes is utilized to measure a blood concentration component (e.g., hemoglobin).

In other embodiments, more than two light sources (e.g., emitters) may be utilized to provide incident light at more than two unique wavelengths. In addition, more than a single photodetector may be utilized in order to measure attributes of the emission response at a plurality of emission wavelengths. Similarly, although a pair of emitters 212a and 212b and a single photodetector 214 are utilized in FIG. 2C, in other embodiments more than two emitters may be utilized along with a plurality of photodetectors. In addition, although each emitter and photodetector is illustrated as a separate entity, in some embodiments the functions of an emitter and photodetector are included in a single element.

Figure 3:
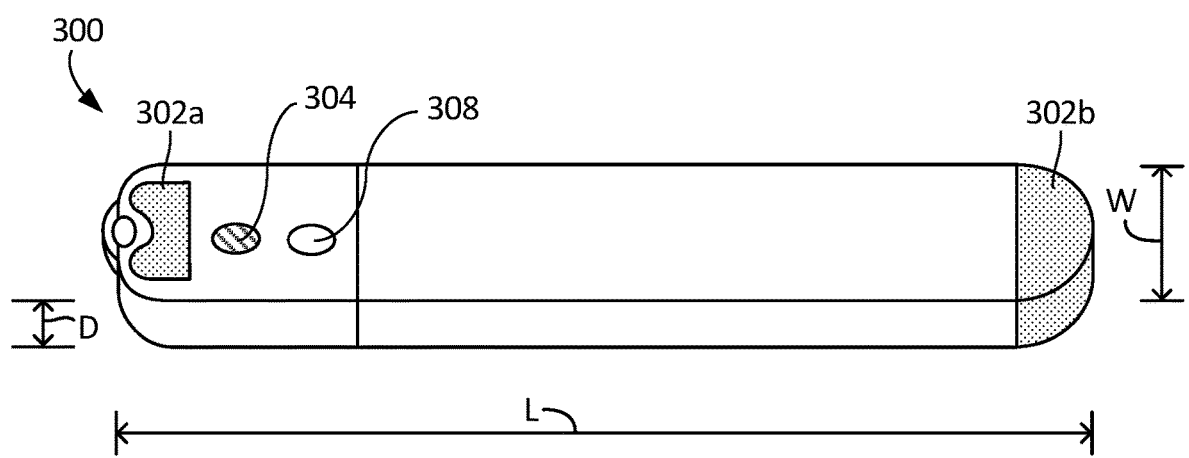
FIG. 3 is a perspective view of an insertable monitoring device according to some embodiments.

FIG. 3 is a perspective view of an insertable monitoring device 300 according to some embodiments. In contrast with an adherent device, which is secured to the skin of a patient, insertable monitoring devices 300 are inserted subcutaneously. Insertable device 300 includes at least first and second electrodes 302a and 302b, at least one emitter 304 and at least one photodetector 308. As discussed above, in order to generate the desired ratio, at least two emitters 304 are required in combination with at least one detector 308, or at least two photodetectors 308 are required in combination with at least emitter 304. For example, in one embodiment insertable monitoring device 300 utilizes first and second photodetectors, each measuring attributes at unique emission wavelengths and at least one emitter providing light at a desired excitation wavelength. In this embodiment, the emission wavelengths selected for first and second photodetectors 308 is based on the particular blood component being analyzed, and are selected to correlate with at least one maximum and at least one minimum of the emission response of the component being monitored. For example, oxyhemoglobin is defined by an emission response that includes a maximum at a wavelength of approximately 575 nm, and a minimum at a wavelength of approximately 560 nm. In one embodiment, first photodetector 308 may be configured to monitor the amplitude of light provided at 575 nm, and second photodetector 308 may be configured to monitor the amplitude of light provided at 560 nm.

Likewise, in another embodiment insertable monitoring device 300 utilizes two or more emitters (i.e., a second emitter in addition to emitter 304) and at least one photodetector 308. In this embodiment, a first emitter provides light at a first excitation wavelength and second emitter provides light at a second excitation wavelength. The first and second emitters are controlled so that incident light is provided at different times. For example, the first emitter may generate incident light for a first period of time, and the second emitter may generate incident light for a second period of time following the first period of time. Photodetector 308 measures one or more attributes associated with the emission response at each of the excitation wavelengths. A ratio is calculated based on the measured attributes and utilized to determine the desired ratio utilized to determine the blood component concentration. A benefit of utilizing ratios is that placement of the insertable device may have an impact on the magnitude of the attributes measured. For example, placement over a vein may increase the absolute value of measured attributes. By utilizing a ratio, variation in absolute values based on placement is mitigated.

Figure 4:
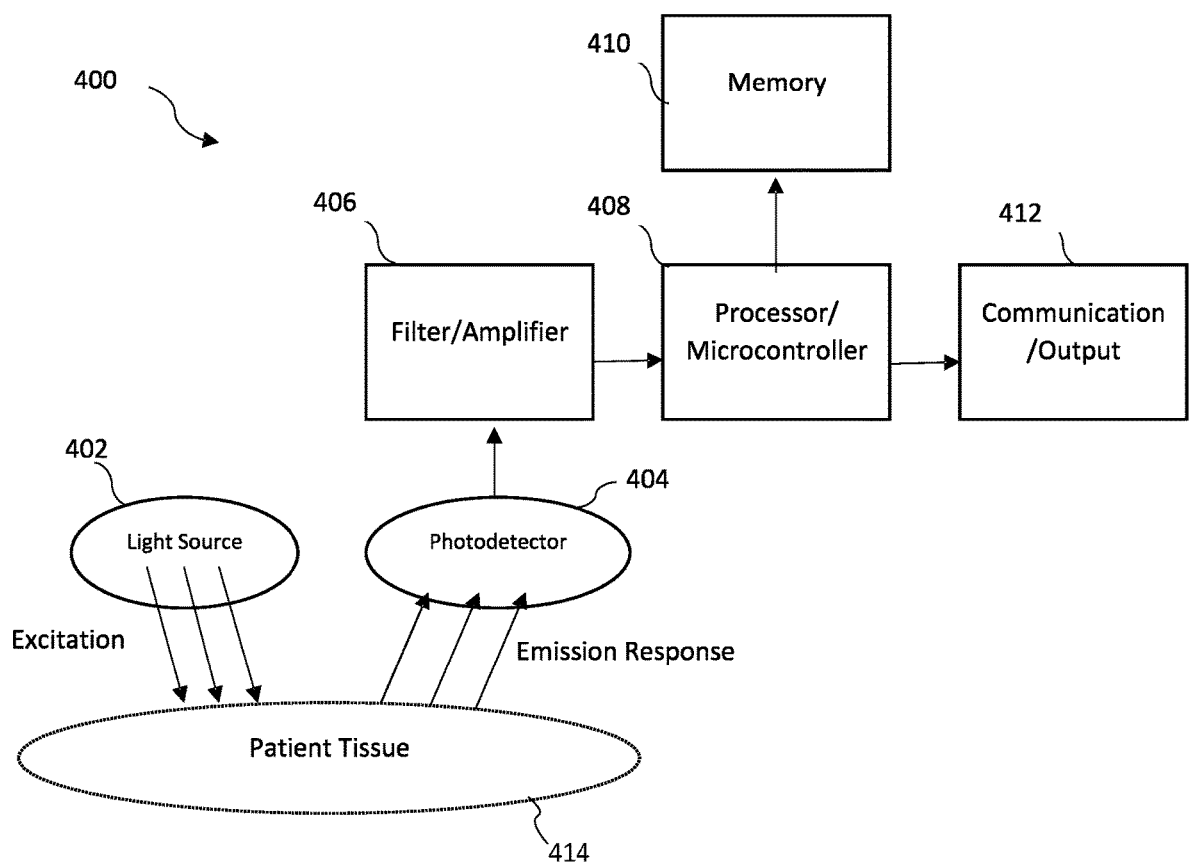
FIG. 4 is a block diagram illustrating components utilized to monitor optical signals and processing optical signals according to some embodiments.

FIG. 4 is a block diagram illustrating components utilized to monitor optical signals and processing optical signals according to some embodiments.

Medical device 400 includes at least one light source 402, at least one detector 404, filter/amplifier 406, processor/microcontroller 408, memory 410, and communication/output 412. As described above, medical device 400 may be adhered to the patient's skin, clipped onto a patient's finger, attached via an arm cuff, inserted subcutaneously, or implanted within the patient. Light source 402 emits light that is provided incident to the patient's tissue, referred to herein as "excitation". In some embodiments, excitation may be provided at a plurality of wavelengths or at a selected wavelength. For example, the wavelength of the emitted light may be selected based on the blood component (e.g., particular protein) to be analyzed, wherein different wavelengths of light interact differently with particular proteins. In some embodiments, light source 402 includes a plurality of light sources each capable of emitting at a particular unique wavelength.

Light from light source 402 interacts with patient tissue 414 or patient fluid, protein or photo-active molecule. The interaction is a result of one or more processes, including autofluorescence, absorption, transmittance and reflectance that results in the emission of light from the tissue, referred to as the emission response. The emission response is detected by the one or more photodetectors 404, which may be place adjacent to the light source 402 (as shown in FIGS. 2B, 2C and 3) or on the opposite side of patient tissue as is common in pulse oximeters. In some embodiments, photodetector 404 may utilize well-known optical sensors, such as complimentary metal-oxide-semiconductor (CMOS) sensor or a charge-coupled device (CCD) sensor. Each of the one or more photodetectors 404 is configured to detect light at a particular emission wavelength. For embodiments in which a plurality of emission wavelengths are monitored, a plurality of photodetectors 404 are required, each configured to monitor one of the desired emission wavelengths. The emission wavelengths monitored by the one or more photodetectors 404 are selected based on the particular blood component being monitored. For example, the emission response morphology (i.e., amplitude of the emission response across the entire wavelength spectrum) depends on how light interacts with the blood component being monitored, with emission responses for each blood component providing different emission response morphology. In particular, emission wavelengths monitored by the one or more photodetectors are selected to correspond with maximum and/or minimum values associated with the emission response spectrum being monitored, or with wavelength(s) of significance on the emission spectrum.

The one or more photodetectors convert the monitored optical signal (i.e., the emission response) to an electrical signal representative of the amplitude of the emission wavelength being monitored. Filter/amplifier 406 filters and amplifies the signal to provide a clean signal to processor/microcontroller 408.

Processor/microcontroller 408 operates in conjunction with memory 410 and communication output 412. In some embodiments, processor/microcontroller 408 provides the measured emission response signals monitored by the photodetectors to an intermediate gateway 102 and/or remote monitoring center 106 (shown in FIG. 1) for subsequent processing. In other embodiments, processor/microcontroller 408 executes instructions locally to perform analysis on the monitored emission response. This may include calculating ratios associated with two or more monitored emission responses, calculating blood component concentrations based on the calculated ratios, comparing the ratios and/or blood component concentrations to threshold values, and/or storing calculated ratios and/or blood component concentrations to memory 410. Results of any analysis performed locally by processor/microcontroller may then be communicated to intermediate device 102, gateway 106, or provided as an alert to the patient (e.g., audio alert).

Figure 5:
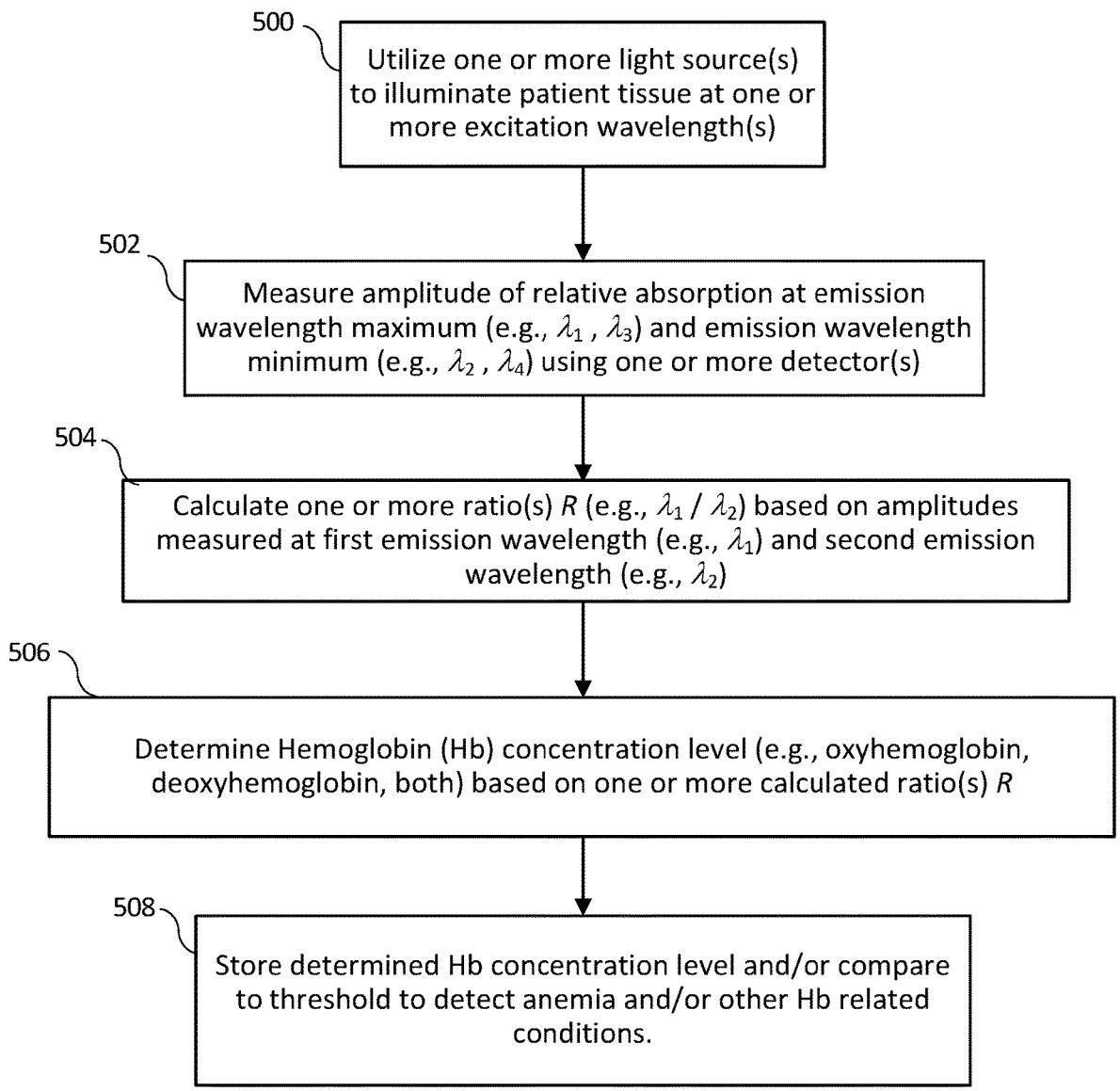
FIG. 5 is a flowchart that illustrates steps utilized to measure hemoglobin concentrations according to some embodiments.
Figure 6:
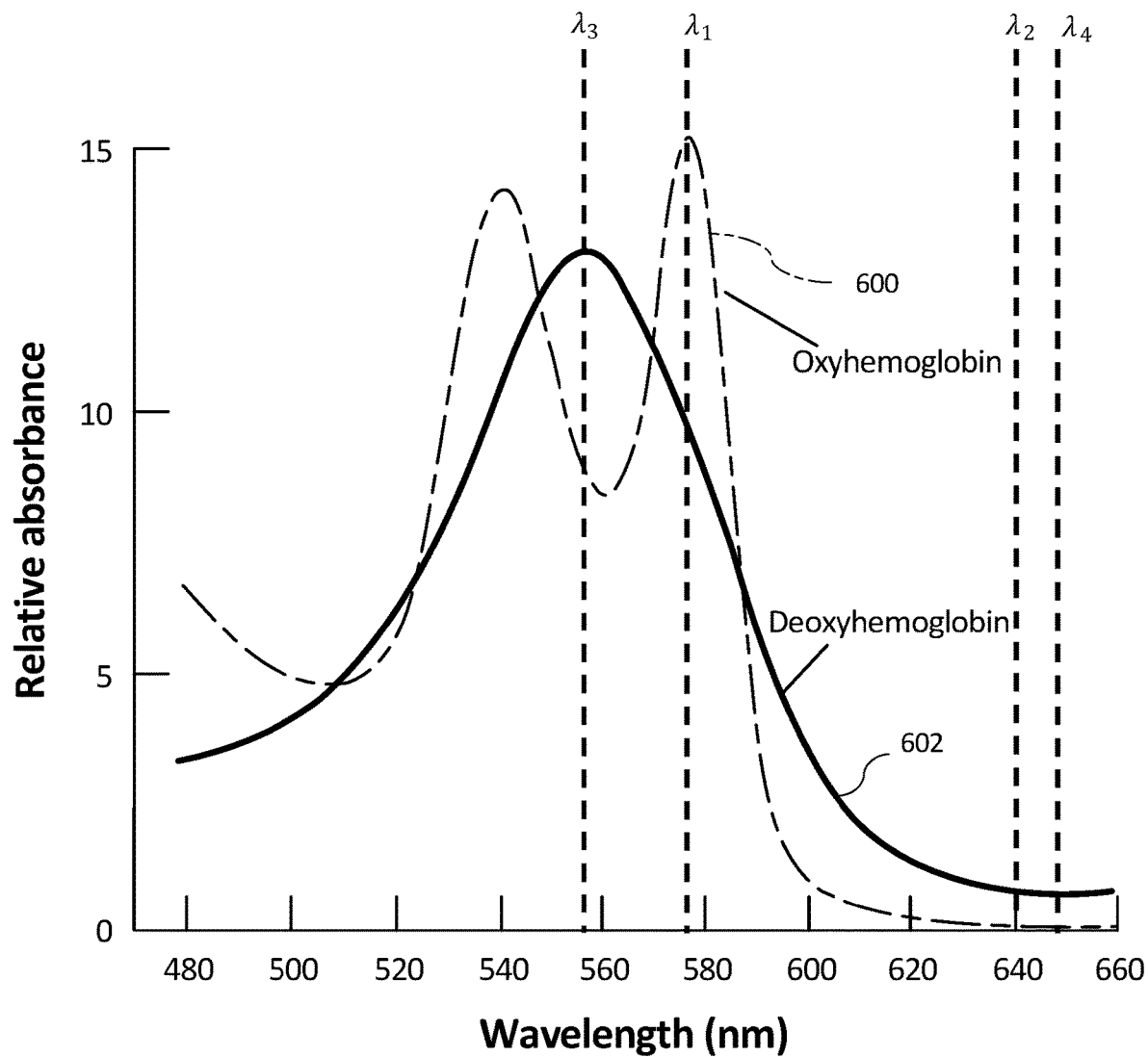
FIG. 6 is a graph that illustrates relative absorbance of hemoglobin at various wavelengths, and minimum and maximum wavelengths utilized to measure hemoglobin concentrations according to some embodiments.

FIG. 5 is a flowchart that illustrates steps utilized to measure hemoglobin concentrations according to some embodiments. Reference is made to FIG. 6, which is a graph that illustrates relative absorbance of oxy-Hb (line 600) and deoxy-Hb (line 602) at various wavelengths, and minimum and maximum wavelengths utilized to measure hemoglobin concentrations according to some embodiments. The change in relative absorbance is a result of changes in the molecular structure when an oxygen molecule is attached to the hemoglobin versus when no oxygen molecule is attached. A typical pulse oximeter utilizes a wavelength in which the relative absorption of oxy-Hb and deoxy-Hb differ significantly and utilizes the measured amplitude to determine the concentration of oxy-Hb to deoxy-Hb. For example, at a wavelength of approximately 660 nm (far right of FIG. 6), the relative absorbance varies significantly between oxy-Hb and deoxy-Hb. Measuring the amplitude of light transmitted at 660 nm and measuring the amplitude of transmitted light allows for a determination to be made regarding concentration of oxy-Hb and/or deoxy-Hb. However, as an absolute measurement, this measurement is highly susceptible to noise and outside influence. For example, a change in ambient light levels will have an effect on the measured amplitude, resulting in errors in the measurement. In contrast, the present invention utilizes minimums and maximums in the known emission response to generate one or more ratios, as discussed in more detail below.

At step 500, one or more light sources are utilized to illuminate patient tissue at one or more excitation wavelengths. In one embodiment, the light source is provided at a wavelength selected based on the blood concentration component to be measured. For example, typically a wavelength is selected in the ultraviolet (UV), visible, or infrared (IR) spectrums in order to generate an absorbance, reflectance, transmittance and/or fluorescence response (i.e., emission response) having the desired spectral morphology. In the embodiment shown in FIGS. 5 and 6, light is provided at a single excitation wavelength (e.g., red visible light, infrared light), but in other embodiments may be provided at a plurality of wavelengths (e.g., visible white light).

In response to the excitation provided by the light source, an emission response is generated that is a function of, at least in part, the concentration of oxy-Hb and deoxy-Hb in the patient's tissue. A full spectrum sweep of each of the wavelengths shown in FIG. 6 and measurement of the resulting emission response is one method of determining the concentration of oxy-Hb and deoxy-Hb, but as discussed above this is prohibitive in terms of computational and battery power requirement. To overcome the cost of a full spectrum wavelength sweep to measure the co ncentration levels of various blood components, wavelength measurements are limited to monitoring two emission wavelengths.

At step 502, first and second photodetectors measure emission at a first wavelength $\lambda_1$ and a second wavelength $\lambda_2$, respectively. The first emission wavelength $\lambda_1$ is selected to correspond with a known maximum of the emission response. For example, in the embodiment shown in FIG. 6, the maximum associated with oxy-Hb occurs at approximately $\lambda_1$ (e.g., wavelength of 578 nm). The second emission wavelength $\lambda_2$ is selected to correspond with a known minimum of the oxy-Hb emission response. For example, in the embodiment shown in FIG. 6, a minimum associated with oxyhemoglobin occurs at approximately any wavelength greater than 620 nm (e.g., 640 nm is selected in this embodiment). If deoxy-Hb is to be monitored, then emission wavelengths are selected that correspond with maximum and minimum values of the deoxy-Hb emission response. For example, an emission wavelength $\lambda_3$ corresponding with a maximum of the deoxy-Hb emission response is selected (e.g., wavelength of approximately 555 nm) and a second emission wavelength $\lambda_4$ corresponding with a minimum of the deoxy-Hb emission response is selected (e.g., wavelength greater than approximately 640 nm, 650 utilized in this embodiment). In some embodiments, the minimum value associated with oxy-Hb and deoxy-Hb may utilize the same emission wavelength (e.g., wavelength of 640 nm).

The measurement taken at step 502 is a measurement of an attribute (e.g., intensity, amplitude, phase, etc.) of the emission response. In general, the photodetector responsible for measuring the attribute at a particular emission wavelength converts the detected light into an electrical signal representative of the measured attribute. In the embodiment shown in FIG. 6, the measured amplitude is analyzed based on relative absorbance spectrum, but may take into account one or more other processes that affect emissions of light from the tissue in response to the incident light. In general, the concentration of blood at any particular time is a combination of oxy-Hb and deoxy-Hb, such that the amplitude measured is a combination of absorbance resulting from the oxy-Hb concentration and the deoxy-Hb concentration. At the minimum wavelength selected (e.g., $\lambda_2$), both oxy-Hb and deoxy-Hb exhibit a relatively low absorbance. In contrast, a large difference in relative absorbance of oxy-Hb and deoxy-Hb is exhibited at the maximum wavelength selected (e.g., $\lambda_1$). This difference in relative absorbance is required in order to utilize the measured amplitudes to determine the relative concentration levels of oxy-Hb and deoxy-Hb. For example, the amplitude of the emission response at wavelength $\lambda_1$ will decrease as the concentration of oxy-Hb concentration increases due to the difference in relative absorbance of oxy-Hb to deoxy-Hb at this wavelength, with oxy-Hb exhibiting greater relative absorbance. However, the emission response at wavelength $\lambda_1$ will also decrease in response to ambient conditions changing, such as the patient walking from an outdoor environment to an indoor environment, which cannot be known simply by measuring the raw amplitude at a particular wavelength, resulting in erroneous determinations of oxy-Hb. To address this change in absolute amplitudes in response to external conditions (e.g., ambient light conditions), one or more ratios are utilized. Other factors that could introduce an error to the absolute raw amplitude include body motion, muscle flexing, circulatory perfusion, movement of the incident light relative to the patient tissue, etc.

At step 504, one or more ratios R are calculated based on the emissions measured at the first and second wavelengths $\lambda_1$ and $\lambda_2$ (e.g., $R_1=\lambda_1/\lambda_2$). The calculated ratio may be calculated on the medical device 100, 110 (shown in FIG. 1), or may be measured at an intermediate device 102 (as shown in FIG. 1) or remotely at a remote monitoring center 106 (as shown in FIG. 1). A benefit of utilizing a ratio R as opposed to an absolute measure at a particular emission wavelength is that use of the ratio R decreases the effect of noise on the measured blood concentration. For example, the effect of changes in ambient light (which also interacts with the patient's tissue) are negated through the use of a ratio of maximum and minimum values. For example, in the embodiment shown in FIG. 6 in which oxy-Hb is being monitored, the ratio R may be calculated based on the amplitude measured at wavelengths $\lambda_1$ divided by the amplitude measured at wavelength $\lambda_2$. A change in ambient light that decreases the amplitude of the emission response at wavelength $\lambda_1$ similarly and proportionally decreases the amplitude of the emission response at wavelength $\lambda_2$.

In one embodiment, the ratio R is defined as the amplitude measured at wavelength $\lambda_1$ divided by the amplitude measured at wavelength $\lambda_2$ (e.g., $R=A_{\lambda 1}/A_{\lambda 2}$). As oxy-Hb concentrations increase, the amplitude measured at wavelength $\lambda_1$ decreases in response to the higher absorption of increasing oxy-Hb concentrations. The amplitude measured at wavelength $\lambda_2$ may increase slightly as deoxy-Hb absorbs more light at wavelength $\lambda_2$, however, the relative absorbance of both oxy-Hb or deoxy-Hb are fairly low at wavelength $\lambda_2$ and therefore the amplitude measured at wavelength $\lambda_2$ will remain relatively unchanged. The net result is a decrease in the ratio R in response to increasing oxy-Hb concentrations. Furthermore, no substantial change in the ratio R results from a change in ambient light. For example, if a patient moves from outdoors (e.g., sunny environment) to indoors, the corresponding decrease in measured amplitudes is relatively the same at wavelengths $\lambda_1$ and $\lambda_2$, resulting in the ratio remaining relatively constant in light of changing ambient conditions.

In other embodiments, various other ratios R may be calculated based on the emission wavelengths measured. For example, the ratio may be defined as the amplitude measured at wavelength $\lambda_3$ (maximum) and wavelength $\lambda_4$ (minimum), which provides information on deoxy-Hb concentration levels. In other embodiments, the ratio may be defined as the amplitude measured at wavelength $\lambda_1$ (oxy-Hb maximum) and wavelength $\lambda_3$ (deoxy-Hb maximum), to provide a ratio of oxy-Hb concentration levels to deoxy-Hb concentration levels.

At step 506, the calculated ratio R is utilized to determine the blood component concentration level (e.g., oxy-Hb concentration, deoxy-Hb concentration, etc.). In one embodiment, the concentration levels may be correlated with various ratios R. For example, the medical device (or remote monitoring center) may include a stored table that correlates measured ratios with concentration levels. In other embodiments, a plurality of ratios may be utilized to determine concentration levels. For example, in the embodiment shown in FIG. 6, a first ratio $R_1$ may be calculated based on the maximum/minimum associated with oxy-Hb and a second ratio $R_2$ may be calculated based on maximum/minimum associated with deoxy-Hb. The plurality of ratios may be utilized alone or in conjunction with one another to determine concentration levels. For example, the combination of ratios $R_1$ and $R_2$ may be utilized to determine the total concentration of hemoglobin (e.g., combination of oxy-Hb and deoxy-Hb).

In one embodiment, determining one or more blood component concentration levels is performed locally by the medical device (e.g., adherent device 100, 200 shown in FIGS. 1 and 2A-2C, monitoring clip 110 shown in FIG. 1, insertable device 300 shown in FIG. 3, etc.). In other embodiment, measured amplitude and/or ratios are communicated to an intermediate device and/or remote monitoring center and determination of concentration levels is performed by the intermediate and/or remote monitoring center.

At step 508, the determined concentration level is stored and/or analyzed to detect patient conditions. For example, in one embodiment the determined concentration level (e.g., hemoglobin concentration level) is compared to a threshold level to detect conditions such as anemia. In some embodiments, the threshold level is an absolute value, while in other embodiments the threshold level is initialized with respect to the patient. For example, to calculate an initialized value, a concentration level may be determined at an initial period (via optical monitoring or via blood test). Having determined an initial value, the threshold level is determined based on the initial value and is utilized to detect conditions such as anemia.

In one embodiment, storage of the concentration level and/or comparison of the concentration level to a threshold level to detect a patient condition is done locally on the medical device (e.g., adherent device, insertable device, etc.). In other embodiments, storage of the concentration level and/or comparison of the concentration level to a threshold level to detect a patient condition is done remotely at an intermediate device and/or remote monitoring center. In response to a detected condition, such as anemia and/or other hemoglobin related conditions, an alert or alarm may be generated and communicated to the patient and/or a monitoring party (e.g., physician, hospital, etc.).

A benefit of the method described in FIGS. 5 and 6 is the ability to provide long-term monitoring of blood component concentration levels. In contrast with typical lab tests, which monitor concentration levels at the instant in time in which blood is drawn, the present invention allows concentration levels to be monitored for long periods of time (e.g., days, weeks). Benefits of long-term monitoring include the ability to detect acute conditions throughout the monitoring period and to alert the patient of the acute condition to reduce the amount of time it takes the patient to receive a diagnosis. Benefits of long-term monitoring further include the ability to average concentration levels over a period of time to account for variations in blood component concentration levels (which vary on short time-tables related to patient heart-beat, as well as longer time tables in response to patient condition). In addition, long-term monitoring allows concentration trends to be detected and utilized to determine whether a condition is improving or worsening. For example, long-term monitoring can be utilized to monitor the efficacy of treatment, and/or monitor progression or worsening of a condition.

Figure 7:
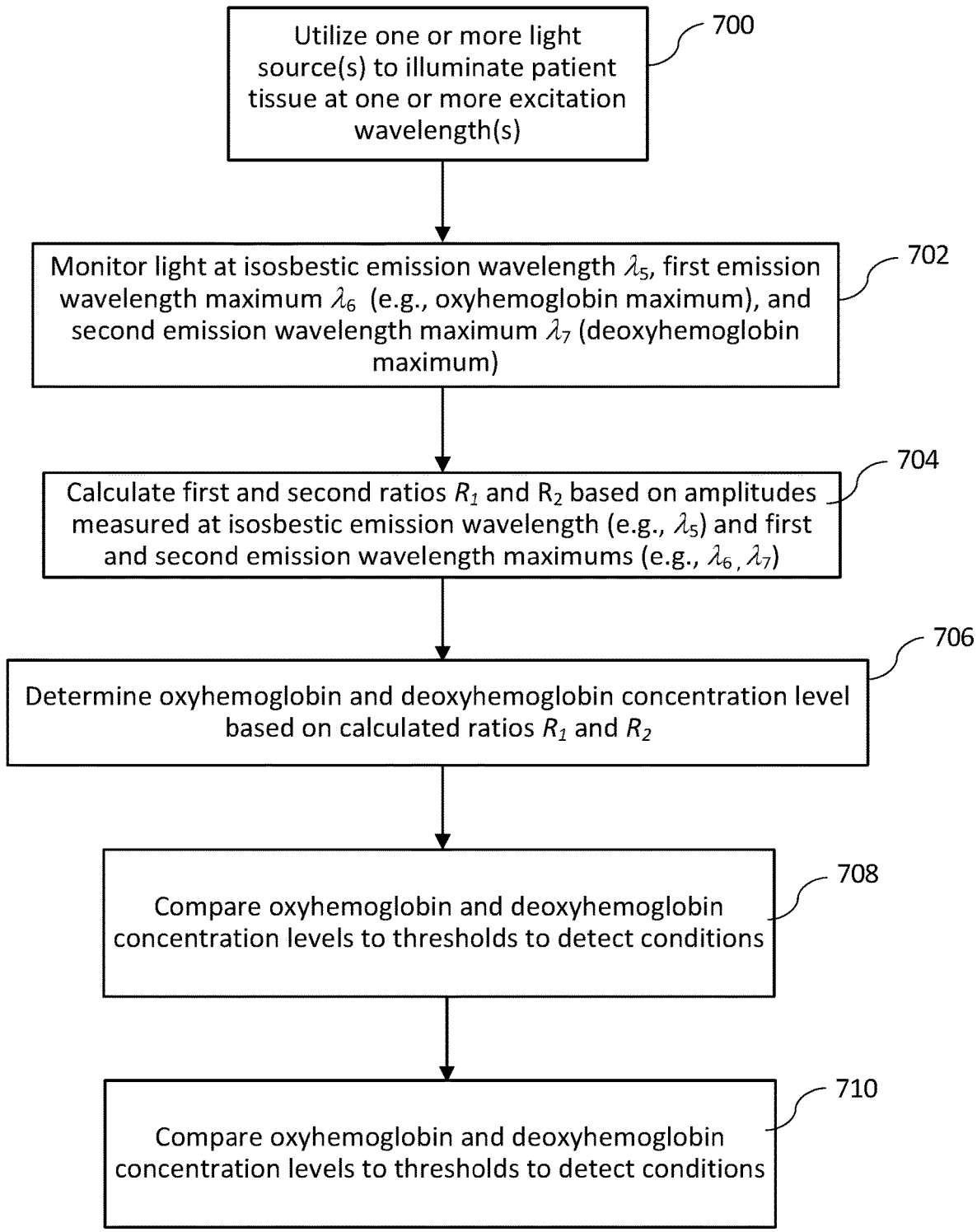
FIG. 7 is a flowchart that illustrates steps utilized to measure hemoglobin concentrations by utilizing an isosbestic wavelength according to some embodiments.

FIG. 7 is a flowchart that illustrates steps utilized to measure hemoglobin concentrations by utilizing an isosbestic wavelength according to some embodiments. FIG. 7 is a graph that illustrates relative absorbance of hemoglobin at various wavelengths, and utilization of an isosbestic wavelength as a minimum for both oxy-Hb and deoxy-Hb maximum wavelengths according to some embodiments.

Figure 8:
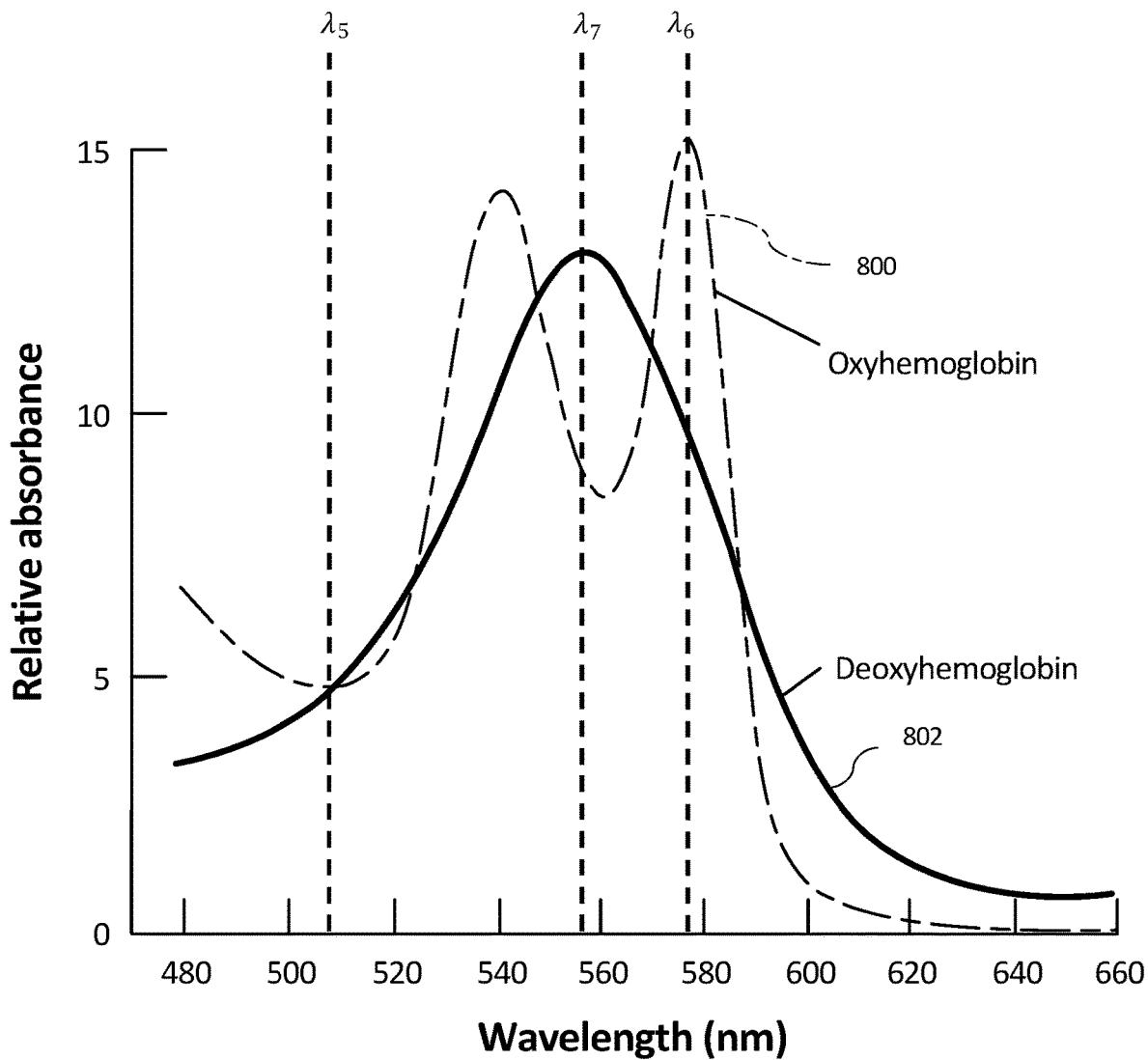
FIG. 8 is a graph that illustrates relative absorbance of hemoglobin at various wavelengths, and utilization of an isosbestic wavelength as a significant wavelength for both oxyhemoglobin and deoxyhemoglobin maximum wavelengths according to some embodiments.

In general, the embodiment shown in FIGS. 7 and 8 is similar to that described with respect to FIGS. 5 and 6. The main difference is in selection of the emission wavelength minima (e.g., the emission wavelength corresponding with an emission response minimum). In contrast with the embodiments shown in FIGS. 5 and 6, in the embodiment shown in FIGS. 7 and 8 the emission wavelength minimum is selected at an isosbestic point that represents a point at which the total absorbance of a sample does not change during a chemical reaction or a physical change of the sample. For example, as illustrated in FIG. 8, an isosbestic point exists at an emission wavelength $\lambda_5$ (e.g., wavelength of approximately 510 nm). At the isosbestic point, the emission response of both oxyhemoglobin (line 800) and deoxyhemoglobin (line 802) are equal to one another. By utilizing an isosbestic point as the emission wavelength minimum, ratios can be calculated for measuring both oxyhemoglobin and deoxyhemoglobin via monitoring of only three emission wavelengths (rather than the four utilized in the embodiment shown in FIGS. 5 and 6).

At step 700, one or more light sources are utilized to illuminate tissue at one or more excitation wavelengths. As discussed above, the excitation wavelength may be selected based on the blood component to be measured (i.e., the excitation wavelength is selected to generate an emission response having the desired morphology). For monitoring blood component concentrations, typically the excitation wavelength utilized is in the visible red spectrum or infrared spectrum. In other embodiments, the light source is provided at a plurality of wavelengths (e.g., white light).

At step 702, one or more photodetectors are utilized to measure emissions at a first wavelength $\lambda_5$, a second wavelength $\lambda_6$, and a third wavelength $\lambda_7$. In some embodiments, only two emission wavelengths need to be monitored in order to measure either oxy-Hb or deoxy-Hb, but in this example three emission wavelengths are monitored and utilized to measure two blood component concentrations. As discussed above, measuring the entire emission response (e.g., measuring at all wavelengths) is prohibitive. However, information about the Oxy-Hb blood component concentration can be determined by measuring the emission response at isosbestic wavelength $\lambda_5$ and a second wavelength $\lambda_6$. The first emission wavelength $\lambda_5$ is selected to correspond with a significant wavelength of the emission response that also corresponds with an isosbestic point between the oxy-Hb emission response and the deoxy-Hb emission response. For example, in the embodiment shown in FIG. 8, an isosbestic point exists at an emission wavelength of approximately 510 nm. In addition to an isosbestic point, second and third emission wavelengths $\lambda_6$ and $\lambda_7$ are selected to correspond with maximums associated with the oxy-Hb emission response and the deoxy-Hb emission response. In the embodiment shown in FIG. 8, the maximum emission response associated with oxyhemoglobin occurs at wavelength $\lambda_6$ (e.g., wavelength of approximately 578 nm, or alternatively a local maximum at 540 nm may be utilized) and the maximum emission response associated with deoxyhemoglobin occurs at wavelength $\lambda_7$ (e.g., wavelength of approximately 555 nm).

The measurement taken at step 702 is a measurement of the intensity/amplitude of the emission response. As discussed above, the photodetector responsible for measuring the amplitude at a particular emission wavelength converts the detected light into an electrical signal representative of the measured amplitude. In the embodiment shown in FIG. 7, the measured amplitude is a measure of the relative absorbance, but may be related to one or more other processes that results in the emission of light from the tissue in response to the incident light.

At step 704, one or more ratios R are calculated based on the emissions measured at the first, second, and third wavelengths $\lambda_5$, $\lambda_6$ and $\lambda_7$. A first calculated ratio $R_1$ is calculated based on first and second wavelengths $\lambda_5$ and $\lambda_6$, and provides information on oxy-Hb concentrations. A second calculated ratio $R_2$ is calculated based on first and third wavelengths $\lambda_5$ and $\lambda_7$, and provides information on deoxy-Hb concentrations. As discussed above, utilizing an isosbestic point allows ratios to be calculated for both oxyhemoglobin and deoxyhemoglobin concentrations via monitoring of three emission wavelengths, rather than four.

At step 706, the calculated ratios $R_1$ and $R_2$ is utilized to determine two or more concentration levels (e.g., oxy-Hb concentration, deoxy-Hb concentration, etc.). In other embodiments, a plurality of ratios may be utilized to determine concentration levels. For example, in the embodiment shown in FIG. 8, a first ratio $R_1$ may be calculated based on the maximum/minimum associated with oxy-Hb and a second ratio $R_2$ may be calculated based on maximum/minimum associated with deoxy-Hb. In this way, measurement of the first and second ratios allows for the discrimination of the two components of hemoglobin and their relative values. The plurality of ratios may be utilized alone or in conjunction with one another to determine concentration levels. For example, the combination of ratio $R_1$ and $R_2$ may be utilized to determine the total concentration of hemoglobin (e.g., combination of oxyhemoglobin and deoxyhemoglobin).

In one embodiment, determining one or more blood component concentration levels is performed locally by the medical device (e.g., adherent device, insertable device, etc.). In other embodiment, measured amplitude and/or ratios are communicated to an intermediate device and/or remote monitoring center and determination of concentration levels is performed by the intermediate and/or remote monitoring center.

At step 708, the determined concentration level is stored and/or analyzed to detect patient conditions. For example, in one embodiment the determined concentration level (e.g., hemoglobin concentration level) is compared to a threshold level to detect conditions such as anemia. In some embodiments, the threshold level is an absolute value, while in other embodiments the threshold level is initialized with respect to the patient. For example, to calculate an initialized value, a concentration level may be determined at an initial period (via optical monitoring or via blood test). Having determined an initial value, the threshold level is determined based on the initial value and is utilized to detect conditions such as anemia.

As discussed above with respect to FIGS. 5 and 6, in some embodiments, storage of the concentration level and/or comparison of the concentration level to a threshold level to detect a patient condition is done locally on the medical device (e.g., adherent device, insertable device, etc.). In other embodiments, storage of the concentration level and/or comparison of the concentration level to a threshold level to detect a patient condition is done remotely at an intermediate device and/or remote monitoring center. In response to a detected condition, such as anemia and/or other hemoglobin related conditions, an alert or alarm may be generated and communicated to the patient and/or a monitoring party (e.g., physician, hospital, etc.).

Figure 9:
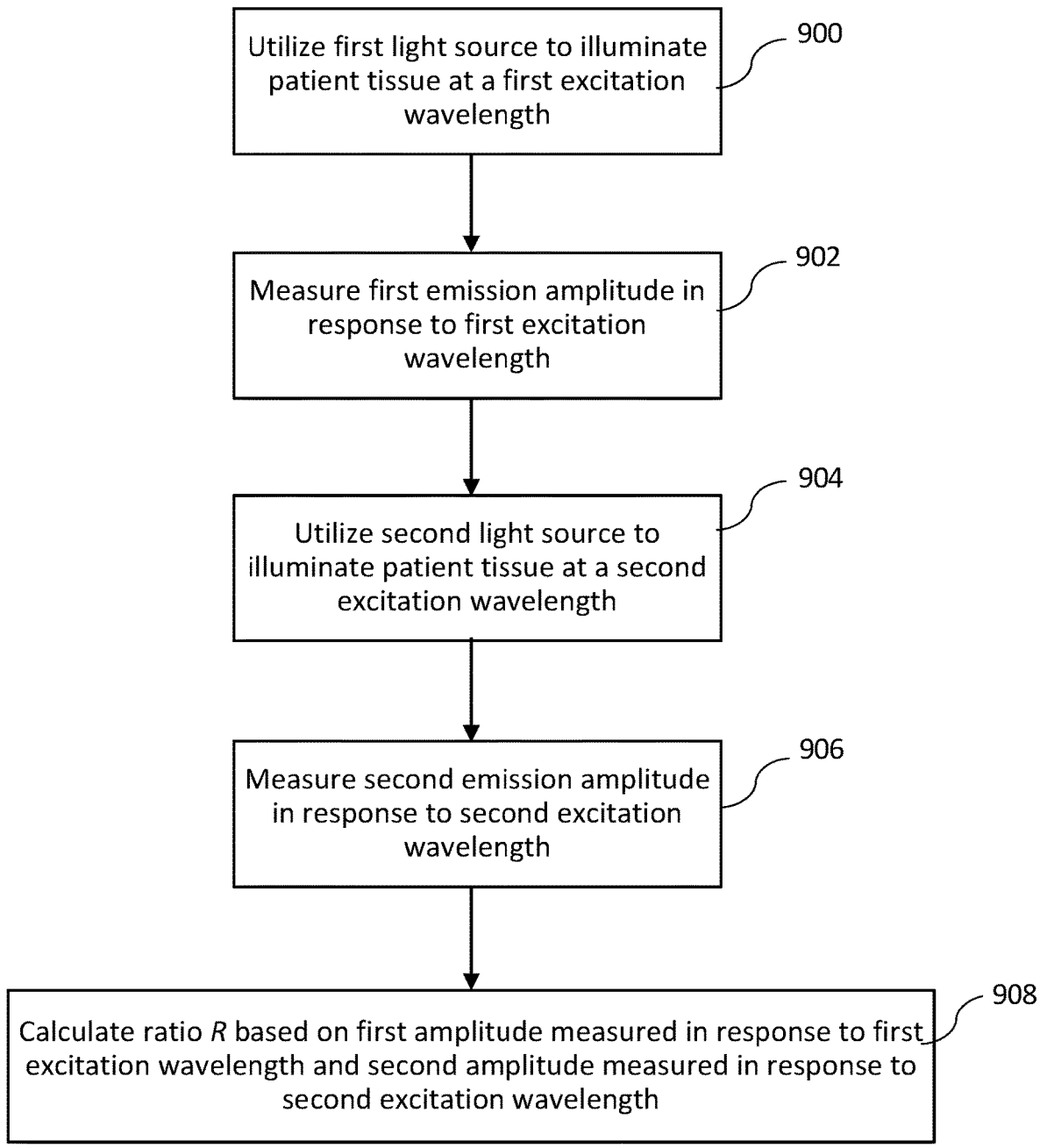
FIG. 9 is a flowchart that illustrates steps utilized to measure hemoglobin concentrations using two light sources and a single detector according to some embodiments.

FIG. 9 is a flowchart that illustrates steps utilized to measure hemoglobin concentrations using two light sources and a single detector according to some embodiments, such as the embodiment shown in FIG. 2C.

At step 900, a first light source is utilized to illuminate patient tissue at a first excitation wavelength. As discussed above, the excitation wavelength may be selected based on the blood component to be measured (i.e., the excitation wavelength is selected to generate an emission response having the desired morphology). For monitoring blood component concentrations, typically the excitation wavelength utilized is in the ultraviolet, visible or infrared spectrum. While the first light source is turned ON or emitting light, the second light source remains OFF, such that only a single light source is emitting light at a given time.

At step 902, at least one photodetector is utilized to measure emissions in response to the first excitation wavelength. In contrast with embodiments described with respect to FIGS. 5-8, in some embodiments only a single emission wavelength is monitored. The emission wavelength utilized by the at least one photodetector is selected to correspond with a known minimum and/or maximum of the emission response associated with the excitation wavelength of the first light source. As discussed above, the emission response may be a result of one or more of tissue absorbance, fluorescence, reflectance, etc., and the emission response morphology (e.g., measured amplitude at all wavelengths) is a result of the excitation wavelength provided by the first light source. Selecting a minimum/maximum along the emission response allows information regarding the blood component being analyzed to be determined without requiring monitoring the entire spectrum of emission wavelengths.

As discussed above, the measurement taken at step 902 is a measurement of the intensity/amplitude of the emission response to the first excitation wavelength. The photodetector responsible for measuring the amplitude at a particular emission wavelength converts the detected light into an electrical signal representative of the measured amplitude.

At step 904, a second light source is utilized to illuminate patient tissue at a second excitation wavelength. As discussed above, the excitation wavelength may be selected based on the blood component to be measured (i.e., the excitation wavelength is selected to generate an emission response having the desired morphology). For monitoring blood component concentrations, typically the excitation wavelength utilized is in the ultraviolet, visible or infrared spectrum. However, both the first excitation wavelength and second excitation wavelengths must be unique in order to generate unique emission responses. With the second light source ON, the first light source is turned OFF, such that only a single light source is emitting light at a given time.

The excitation wavelength of the second light source is selected based on the blood component to be measured, such that the emission response provides the desired morphology. However, whereas the first excitation wavelength was selected to generate an emission response having a maximum at the monitored emission wavelength, the second excitation wavelength is selected to generate an emission response providing something other than a maximum at the monitored emission wavelength, preferably a minimum, based on the blood component concentration to be measured.

At step 906, the at least one photodetector is utilized to measure emissions in response to the second excitation wavelength. In this embodiment, because it is the excitation wavelength that is being modified—not the emission or monitored wavelength—it is important that the emission wavelength monitored by the at least one photodetector be selected to correspond with a maximum associated with the first excitation wavelength and a minimum or value relatively close to a minimum at the second excitation wavelength. In other embodiments, a second photodetector may be utilized that measures emissions at a second wavelength. However, for purposes of the embodiment shown in FIG. 8, only a single emission wavelength is measured.

At step 908, a ratio R is calculated based on the amplitude measured at the first emission wavelength measured in response to first excitation wavelength and the amplitude measured at the first emission wavelength in response to the second excitation wavelength. As discussed above, the ratio represents the relationship between the amplitude measured with respect to the maximum of the emission response and the amplitude measured with respect to the minimum of the emission response. Utilizing this type of ratio allows external effects such as ambient light and noise to be minimized and allows for accurate determination of blood component concentration levels without requiring monitoring of the entire spectrum of emission wavelengths.

Figure 10:
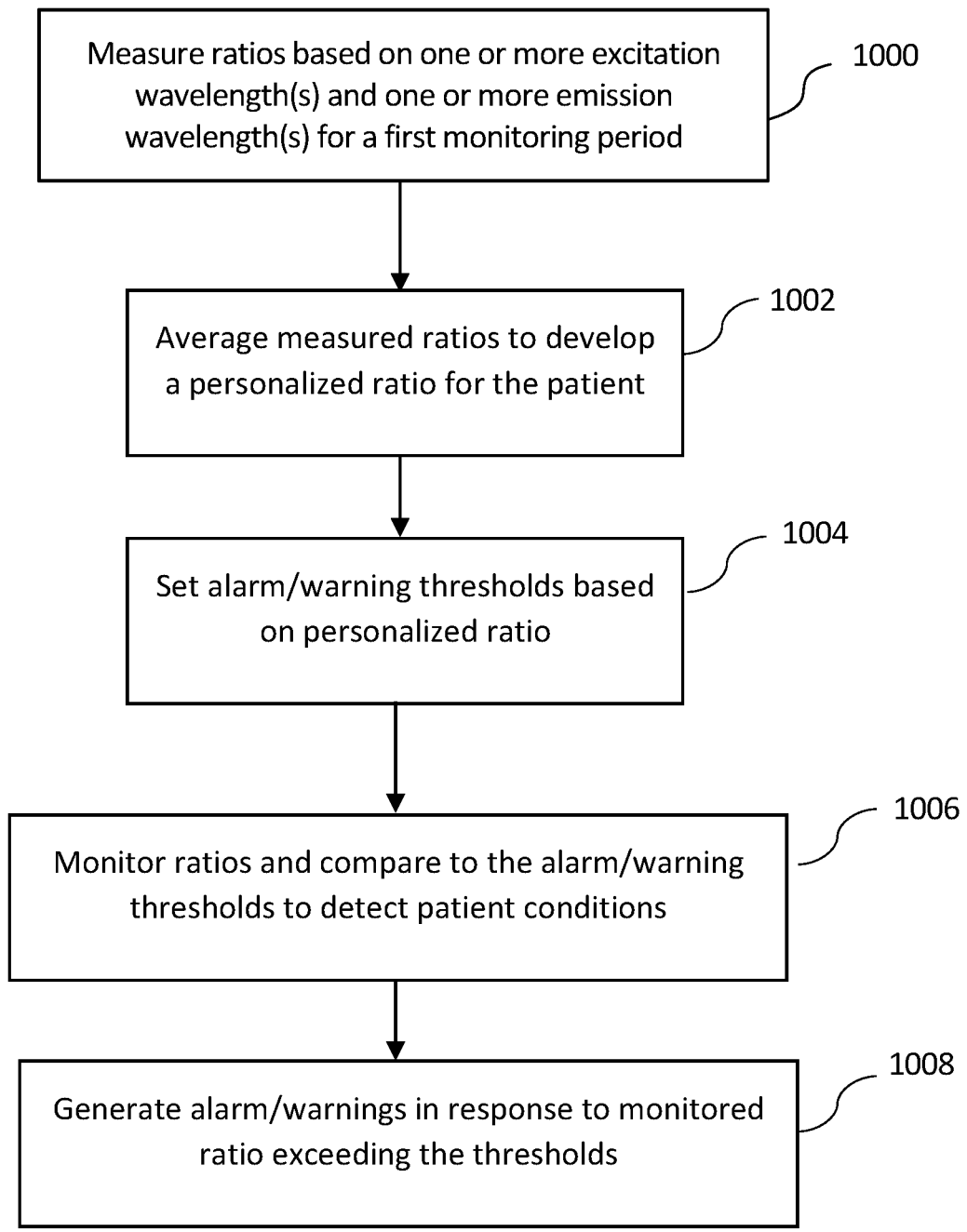
FIG. 10 is a flowchart that illustrates long-term monitoring and storage of hemoglobin concentrations and one or more physiological signals to detect patient conditions according to some embodiments.

FIG. 10 is a flowchart that illustrates long-term (e.g., chronic) monitoring and storage of hemoglobin concentrations and one or more physiological signals to detect patient conditions.

At step 1000, a plurality of ratios are measured based on first and second amplitudes measured by one or more photodetectors over a first monitoring period (e.g., initialization period). A single light source may be utilized along with multiple photodetectors associated with multiple emission wavelengths, or a plurality of light sources may be utilized at two or more excitation wavelengths, along with one or more photodetectors associated with one or more emission wavelengths. In general, at least one of the emission wavelengths is selected to correspond with a maximum of the emission response and at least one of the emission wavelengths is selected to correspond with a minimum of the emission response. This may be accomplished by selecting by properly selecting the emission wavelength(s) and/or properly selecting the excitation wavelength(s).

The initialization period requires a period of time long enough to determine a baseline of the blood concentration value to be monitored. This may mean several minutes of monitoring, or several days of monitoring. A plurality of ratio measurements are taken during the monitoring period, allowing for averages and deviations associated with the blood concentration value to be monitored. A benefit of utilizing an initialization period, is measurements may vary from patient to patient based on factors such as device placement—including general placement as well as factors such as placement adjacent to a blood vessel—body type of the patient, skin color, etc. Each of these factors may modify how light interacts with the patient and the resultant emission response from the patient.

In one embodiment, a plurality of unique ratios are collected in order to monitor different blood concentration levels (e.g., oxyhemoglobin, deoxyhemoglobin, etc.). For example, a first unique ratio may be related to oxy-Hb levels, and at step 1000 a plurality of measurements are taken during the first monitoring period with respect to the first unique ratio. A second unique ratio may be related to deoxy-Hb levels, and at step 1000 a plurality of measurements may be taken during the first monitoring period with respect to the second unique ratio.

At step 1002, for each unique ratio monitored, the plurality of ratios corresponding with each unique ratio measured during the first monitoring period are averaged to develop a personalized ratio for the patient. For example, a plurality of ratios associated with oxyhemoglobin concentration levels taken during the initialization period are averaged utilized to generate a baseline or initial ratio representing the average oxyhemoglobin level of the patient. The personalized ratio may represent a true averaging of the oxyhemoglobin levels, a mean of the monitored ratios, or other statistical tools utilized to determine a personalized ratio value or values.

At step 1004, the personalized ratio is utilized to set alarm/warning thresholds. In one embodiment, the threshold may be calculated at a predefined magnitude above and/or below the personalized ratio. For example, a personalized ratio related to oxy-Hb concentration (e.g., oxygenated blood) may result in a threshold being set at fixed amounts above and below the personalized ratio, creating a monitoring envelope around the personalized ratio. In other embodiments, rather than a predetermined or fixed threshold above and/or below the personalized ratio, the envelope is defined by statistical tools such as standard deviation. In other embodiment, the threshold is defined by a percentage change in the personalized ratio, and in other embodiments may be defined by a rate of deviation from the personalized ratio (e.g., warning threshold reached if oxy-Hb levels change rapidly from a personalized ratio). For each personalized ratio monitored, an individual monitoring envelope may be created.

At step 1006, one or more ratios are monitored and compared to the alarm/warning thresholds to detect patient conditions. The one or more ratios may be individual measurements, or may be based on averaging as well. For example, if ratio related to hemoglobin concentrations fall below a threshold value, this is an indication that the person may be anemic or experiencing blood loss, and requires medical attention. In other embodiments, the ratio may be monitored for changes from an initial value (e.g., percentage change), rate of change, etc.

At step 1008, an alert is generated in response to the monitored ratio exceeding or falling below one or more of the thresholds. In some embodiments, when a threshold is crossed, this triggers additional measurements in order to confirm the accuracy of the result. This may include increasing the frequency at which readings are taken, or simply continuing to monitor to ensure that the measured ratios are accurate.

The alert may be provided to the patient in the form of an audio or visual alert. The alert may also be communicated to the intermediate gateway 102 or remote monitoring center 106 (shown in FIG. 1). The alert may be provided to a physician or expert for analysis and confirmation of the detected patient condition.

One of the benefits of the embodiment described with respect to FIG. 10, in combination with adherent and/or insertable devices is that they allow for long-term monitoring of trends in blood concentration levels. In particular, the utilization of ratios minimizes the effect of external influences and noise (such as changing ambient light conditions, etc.), and initialization of the ratio to an average value monitored over an initial monitoring period allows the ratios to be personalized for each patient (to account for differences in the physiology of each patient).

Figure 11:
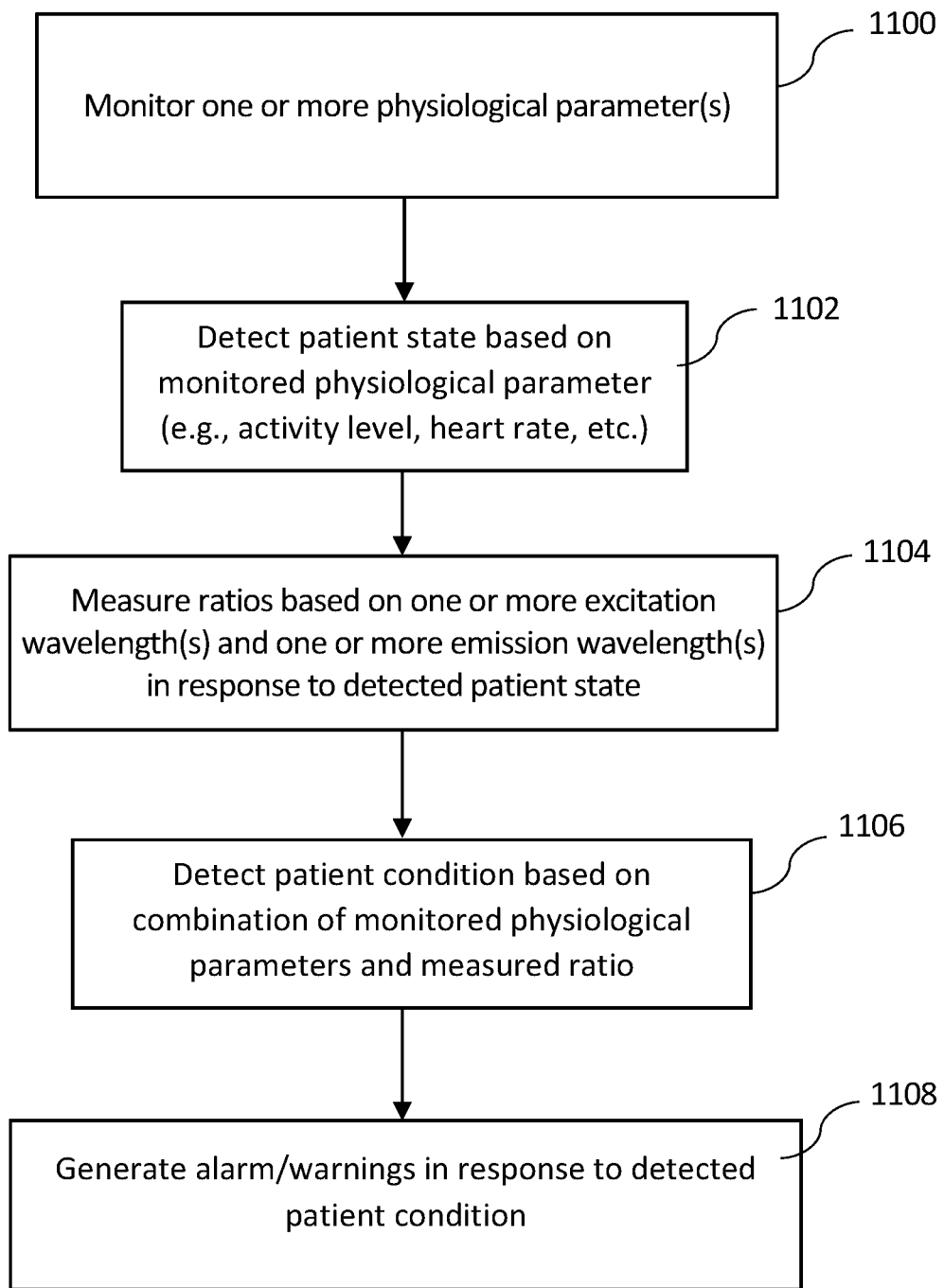
FIG. 11 is a flowchart that illustrates dynamic monitoring and storage of hemoglobin concentrations and one or more physiological signals to detect patient conditions according to some embodiments.

FIG. 11 is a flowchart that illustrates dynamic monitoring and storage of hemoglobin concentrations and one or more physiological signals to detect patient conditions. In this embodiment, one or more physiological parameters are measured and utilized to determine a patient state that triggers measurement of one or more ratios related to blood concentration levels.

At step 1100, one or more physiological parameters are monitored. Examples of physiological parameters being monitored include ECG related signals (e.g., heart rate), bioimpedance, respiration rates, activity level, and/or posture.

At step 1102, patient states are detected based on the one or more physiological parameters. For example, patient states may include heart-related patient states, such as various arrhythmic states (e.g., tachycardia, bradycardia, etc.), active or resting states (based on posture, respiration rates, heart rate, activity level, etc.), and others. Depending on the patient state detected, it may be beneficial to monitor one or more ratios related to one or more blood concentration levels (e.g., oxyhemoglobin, deoxyhemoglobin, etc.). For example, for heart failure patients, it may be important to monitor oxy-Hb levels while the patient is exercising to ensure they do not fall below threshold levels. The one or more physiological signals are utilized to detect that a patient is exercising (e.g., based on one or more of posture, heart rate, breathing rate, activity level, etc.). In response to a detected activity level, optical signals are generated and emissions measured to calculate a ratio related to oxyhemoglobin concentration levels. One of the benefits of increasing the level of optical monitoring or triggering optical monitoring based on patient state, is resources (battery, memory, processing bandwidth, data transmission, etc) are conserved until it is useful to monitor.

At step 1104, one or more excitation sources are utilized to illuminate tissue and one or more emission wavelengths are monitored to detect one or more ratios related to one or more blood concentration levels.

At step 1106, a patient state is determined based on the one or more measured ratios and one or more physiological parameters. For example, if it is determined that the patient is exercising, and the monitored ratio indicates that oxyhemoglobin concentrations have fallen below a threshold value, this may indicate a dangerous condition for a patient with heart failure. In response to detecting a condition such as this, at step 1108, an alert is generated and provided to the patient. The alert may indicate the detected condition, and may provide instructions to the patient on mitigating the risk. In other embodiments, the alert may be communicated to an intermediate device 102 and/or remote monitoring center for review by a physician/technical expert.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for non-invasive monitoring of hemoglobin concentration level, the system comprising:
    a medical device comprising:
        at least one light source configured to provide light to patient tissue;
        a first photodetector configured to monitor an emission response at a first emission wavelength, wherein the first emission wavelength is selected to correspond with a maximum of the emission response of a hemoglobin component, wherein the hemoglobin component comprises at least one of oxyhemoglobin or de-oxyhemoglobin; and
        a second photodetector configured to monitor the emission response at a second emission wavelength, wherein the second emission wavelength is selected to correspond with a minimum of the emission response of the hemoglobin component; and
    one or more processors configured to receive the emission responses at the first emission wavelength and the second emission wavelength, wherein the one or more processors are configured to calculate a ratio based on the received emission responses and utilize the calculated ratio to determine the hemoglobin concentration level.

2. The system of claim 1, wherein the hemoglobin component is oxyhemoglobin and the hemoglobin concentration level is an oxyhemoglobin concentration level, wherein the first emission wavelength is selected to correspond with a maximum of an oxyhemoglobin emission response and the second emission wavelength is selected to correspond with a minimum of the oxyhemoglobin emission response.

3. The system of claim 1, wherein the hemoglobin component is de-oxyhemoglobin and the hemoglobin concentration level is a de-oxyhemoglobin concentration level, wherein the first emission wavelength is selected to correspond with a maximum of a de-oxyhemoglobin emission response and the second emission wavelength is selected to correspond with a minimum of the de-oxyhemoglobin emission response.

4. The system of claim 1, wherein the one or more processors are configured to control generation of an alert in response to the hemoglobin concentration level falling below a threshold value, indicating anemia or change in the hemoglobin component.

5. The system of claim 1, wherein the hemoglobin concentration level is determined in real-time or near real-time by the one or more processors.

6. The system of claim 1, wherein the one or more processors are configured to collect and store a plurality of determined hemoglobin concentration levels over a first monitoring period, and provide an output of trends in monitored hemoglobin concentration levels.

7. The system of claim 1, wherein the medical device further includes sensors for monitoring physiological parameters associated with the patient, including one or more of electrocardiogram (ECG) signals, respiration rates, bio-impedance levels, activity level, postures, or temperature.

8. The system of claim 7, wherein the one or more processors are configured to utilize at least one of the monitored physiological parameters in combination with stored hemoglobin concentration levels to determine a patient condition.

9. The system of claim 1, wherein the hemoglobin component comprises a first hemoglobin component and the ratio comprises a first ratio, the system further comprising a third photodetector configured to monitor the emission response at a third emission wavelength, wherein the third emission wavelength is selected to correspond with a maximum of the emission response of a second hemoglobin component, and wherein the one or more processors are configured to:
    receive the emission response at the third emission wavelength;
    calculate a second ratio based on the third emission response; and
    determine the hemoglobin concentration level based on a combination of the first ratio and the second ratio.

10. A method of non-invasively monitoring hemoglobin concentration level, the method comprising:
    providing incident light to patient tissue at a first excitation wavelength;
    monitoring an emission response at a first emission wavelength, wherein the first emission wavelength is selected to correspond with a maximum of the emission response of a hemoglobin component, wherein the hemoglobin component comprises at least one of oxyhemoglobin or de-oxyhemoglobin;
    monitoring the emission response at a second emission wavelength, wherein the second emission wavelength is selected to correspond with a minimum of the emission response of the hemoglobin component; and
    calculating the hemoglobin concentration level based on a ratio of the emission response measured at the first emission wavelength to the emission response measured at the second emission wavelength.

11. The method of claim 10, wherein the hemoglobin component is oxyhemoglobin and the hemoglobin concentration level is an oxyhemoglobin concentration level, wherein the first emission wavelength is selected to correspond with a maximum of an oxyhemoglobin emission response and the second emission wavelength is selected to correspond with a minimum of the oxyhemoglobin emission response.

12. The method of claim 10, wherein the hemoglobin component is de-oxyhemoglobin and the hemoglobin concentration is a de-oxyhemoglobin concentration, wherein the first emission wavelength is selected to correspond with a maximum of a de-oxyhemoglobin emission response and the second emission wavelength is selected to correspond with a minimum of the de-oxyhemoglobin emission response.

13. The method of claim 10, further including detecting anemia based on the calculated hemoglobin concentration level falling below a threshold level.

14. The method of claim 10, wherein the monitoring and calculating a hemoglobin concentration level is performed in real-time or near real-time.

15. The method of claim 10, further including monitoring physiological parameters associated with the patient, including one or more of electrocardiogram (ECG) signals, respiration rates, bio-impedance levels, activity level, postures, or temperature.

16. The method of claim 15, further including utilizing at least one of the monitored physiological parameters in combination with stored hemoglobin concentration levels to determine a patient condition.

17. The method of claim 10, wherein the hemoglobin component comprises a first hemoglobin component and the ratio comprises a first ratio, the method further comprising:
monitoring the emission response at a third emission wavelength, wherein the third emission wavelength is selected to correspond with a maximum of the emission response of a second hemoglobin component; and
calculating a second ratio based on the third emission response; and
wherein calculating the hemoglobin concentration level comprises calculating the hemoglobin concentration level based on a combination of the first ratio and the second ratio.

* * * * *